United States Patent [19]

Macrae

[11] Patent Number: 4,956,286

[45] Date of Patent: Sep. 11, 1990

[54] PROCESS FOR THE PREPARATION OF ESTERS

[75] Inventor: Alasdair R. Macrae, Bedford, Great Britain

[73] Assignee: Unilever Patent Holdings B.V., Rotterdam, Netherlands

[21] Appl. No.: 135,355

[22] Filed: Dec. 21, 1987

[30] Foreign Application Priority Data

Dec. 19, 1986 [EP] European Pat. Off. ........ 86202336.3

[51] Int. Cl.$^5$ ............................ C12N 9/20; C12P 7/64
[52] U.S. Cl. .................................... 435/134; 435/271; 435/198
[58] Field of Search ..................... 435/134, 198, 271

[56] References Cited

U.S. PATENT DOCUMENTS

| | | | |
|---|---|---|---|
| 4,275,011 | 6/1981 | Tanaka et al. | 435/134 |
| 4,275,081 | 6/1981 | Coleman et al. | 435/134 |
| 4,377,686 | 3/1983 | Feuge et al. | 536/119 |
| 4,735,900 | 4/1988 | Urata et al. | 435/134 |

*Primary Examiner*—Ronald W. Griffin
*Assistant Examiner*—Pamela S. Webber
*Attorney, Agent, or Firm*—Cushman, Darby & Cushman

[57] ABSTRACT

The invention provides a process for preparing an ester from an alcohol and fatty acid (glyceride) by enzyme-catalyzed conversion, in which a fatty acid (glyceride) and alcohol are contacted with lipase and the alcohol is added at such a rate that the alcohol concentration in the reaction mixture is kept below a molar ratio of 0.5 moles of alcohol per mole of fatty acid/acyl group, preferably below 0.25. The alcohol is a $C_1$–$C_8$ alcohol, preferably a monohydric alcohol. The fatty acid is a $C_2$–$C_{24}$ fatty acid, preferably a $C_{10}$–$C_{24}$ fatty acid. Preferably, water of reaction is removed while esterification progresses.

11 Claims, No Drawings

PROCESS FOR THE PREPARATION OF ESTERS

This invention relates to a process for preparing an ester from an alcohol and fatty acid (glyceride) by enzyme-catalyzed conversion.

The preparation of fatty acid esters from fatty acid/glyceride starting material using an enzyme-catalyzed reaction is well known.

British Specification No. (GB-A-) 1 577 933 (Unilever) discloses interesterification of a fatty acid glyceride with another triglyceride containing moieties of different fatty acids or a fatty acid employing a lipase enzyme catalyst and an amount of water.

There is a disclosure of the preparation of an ester from alcohol and a fatty acid by enzyme-catalyzed reaction, viz U.S. Pat. No. (US-A) 4,451,565 (Haarmann & Reimer), disclosing, inter alia, the esterification of oleic acid with ethanol in the presence of lipase.

It is not clear from this specification how the reactants were brought into contact with each other.

It has now been found that the rate at which the desired ester is formed can be increased considerably if fatty acid (glyceride) and the alcohol are contacted with lipase and the alcohol is added at such a rate that the alcohol concentration in the reaction mixture is kept below a molar ratio of 0.5 moles of alcohol per mole of fatty acid/acyl group. Preferably this ratio is kept below 0.25.

The fatty acid (glyceride) starting material is $C_2-C_{24}$ saturated or unsaturated monocarboxylic acid with preferably a straight chain or a glyceride thereof, preferably a triglyceride. Such triglycerides are abundantly available as animal or vegetable oils and fats. Soybean oil, coconut oil, butter oil etc. are very suitable.

The alcohol component is a $C_1-C_8$ alcohol, preferably a monohydric alcohol, and $C_2-C_4$ primary alcohols are preferred. Ethanol and isopropanol are very suitable. Polyalcohols such as glycols can also be used.

The lipase used according to the invention is usually of microbial origin and enzyme material obtained from *Mucor miehei*, Rhizopus species, *Aspergillus niger*, *Candida cylindracae*, Pseudomonas species or Arthrobacter species can be used.

The enzyme can be used as such, i.e. in some purified form, but preferably it is attached to some carrier material like diatomaceous earth so that it can be separated after reaction and re-used. Enzymes can be immobilized by various techniques such as absorption on carrier, attachment to ion exchange resins, covalent bond attachment to supports, trapping in hydrophobic gels etc.

For efficient use of the enzyme, it is desirable that some water should be present during the ester formation; however, water also tends to hydrolyze the ester so that only very small amounts are desirable, in particular amounts which dissolve in the starting mixture. When water of reaction is formed as the reaction progresses, as is the case when fatty acid is reacted with alcohol, it is desirable that excess water should be removed during the reaction, e.g. by dipping a cold surface in the headspace of the reaction vessel (allowing the water to freeze out), or, alternatively, by distillation at a relatively low temperature at which the lipase is still active, especially under reduced pressure. Alternatively, water can be absorbed, e.g. by molecular sieve material added.

The ester forming reaction is usually carried out in a temperature range between 10° and 90° C., preferably between 30° and 70° C. The reaction normally takes at least several hours.

The alcoholysis should be carried out continuously (stirred tank) or semi-continuously (cascade method) or batchwise. The lipase is separated from the reaction mixture and normally re-used.

The invention is illustrated by the following Examples.

EXAMPLE 1

10 mmoles of oleic acid (2.82 g) were stirred at 40° C. with 40 mg of lipase catalyst consisting of *Mucor miehei* lipase supported on diatomaceous earth particles. The catalyst was supplied by Novo Industri and dried under vacuum at 30° C. prior to use. The catalyst contained 9100 lipase units per gram (1 lipase unit releases 1 $\mu$ mole of fatty acid per minute at pH 7.0 and 30° C. from a 5% emulsion of glycerol tributyrate in 0.6% gum arabic solution).

To initiate an esterification reaction, 2.0 mmoles (116 $\mu$l) of ethanol were added to the mixture of oleic acid and catalyst. Seven further 1.15 mmoles (67 $\mu$l) aliquots of ethanol were added hourly intervals to give a total ethanol addition of 10 mmoles. Samples were taken periodically from the reaction mixture for analysis of ethanol content and ethyl oleate formation by gas chromatography.

In a control experiment the entire 10 mmoles of ethanol were added to the mixture of oleic acid and catalyst at the start of the reaction. Again samples were taken periodically for analysis.

The results given in Table 1 clearly show that ethyl oleate was formed more rapidly in the experiment, in which the ethanol was added in small aliquots to ensure that the ethanol concentration in the reaction mixture remained low. In this experiment ester formation was substantially complete after 12 hours (the maximum attainable yield of ester is approximately 7 mmoles).

TABLE 1

| Reaction time (hours) | Ethyl oleate formed | | Ethanol content of reaction mixture | |
|---|---|---|---|---|
| | Example 1 (mmoles) | Control (mmoles) | Example 1 (mmoles) | Control (mmoles) |
| 2 | 1.62 | 0.37 | 1.5 | 9.6 |
| 4 | 3.21 | 0.79 | 2.2 | 9.2 |
| 6 | 4.46 | 1.28 | 3.3 | 8.7 |
| 8 | 5.32 | 1.61 | 4.7 | 8.4 |
| 12 | 6.40 | 2.47 | 3.6 | 7.5 |
| 24 | 6.73 | 6.41 | 3.3 | 3.6 |

EXAMPLE 2

100 g of butter oil (0.141 moles) were stirred at 40° C. with 2.5 g of the catalyst described in Example 1. Ethanol was pumped gradually into the reaction mixture at a rate of 2.06 ml hr$^{-1}$ for 8 hours to give a total ethanol addition of 16.5 ml (0.282 moles). Samples were taken periodically from the reaction mixture for analysis of the lipid products by high performance liquid chromatography.

In a control experiment 16.5 ml of ethanol were added in one aliquot to the mixture of butter oil and catalyst at the start of the reaction. Again samples were taken periodically for analysis.

The results shown in Table 2 demonstrate that ethyl esters were formed more rapidly in the experiment in which the ethanol was pumped gradually into the reaction mixture. In this experiment the ethanol content of the reaction mixture was low, reaching a maximum level of 0.14 mole after eight hours.

TABLE 2

| Reaction time (hours) | Amount of ethyl esters in lipid products | |
|---|---|---|
| | Example 2 (%) | Control (%) |
| 2.0 | 14.6 | 4.1 |
| 4.1 | 26.1 | 9.6 |
| 6.0 | 30.6 | 13.1 |
| 8.0 | 33.6 | 16.8 |

EXAMPLE 3

100 g of coconut oil (0.150 moles) were stirred at 40° C. with 2.5 g of the catalyst described in Example 1. Ethanol was pumped gradually into the reaction mixture at a rate of 1.03 ml hr$^{-1}$ for 24 hours to give a total ethanol addition of 24.7 ml (0.424 moles). Samples were taken periodically for analysis of the reaction products.

In a control experiment 24.7 ml of ethanol were added in one aliquot to the mixture of coconut oil and catalyst at the start of the reaction. The product formed after 24 hours were analysed.

The results given in Table 3 again show that the ethyl esters were formed more rapidly in the experiment in which ethanol was gradually added to the reaction mixture. In this experiment the ethanol content of the reaction mixture reached a maximum level of 0.22 moles after 24 hours' reaction.

TABLE 3

| Reaction time (hours) | Amount of ethyl esters in lipid products | |
|---|---|---|
| | Example 3 (%) | Control (%) |
| 6.0 | 18.7 | — |
| 10.0 | 27.7 | — |
| 24.0 | 43.6 | 20.0 |

EXAMPLE 4

An immobilised lipase catalyst was prepared using *Candida cylindracae* lipase and Dualite ES 568 ion exchange resin. Lipase MY, ex Meito Sangyo Co. Ltd, was dissolved in 0.1M potassium phosphate buffer pH 6.0 to give a solution containing 1,400 lipase units ml$^{-1}$. 79 ml of this solution was stirred with 8.0 g of the above resin at room temperature for 4 hours. Adsorption of the lipase onto the resin particles occurred, and immobilised lipase catalyst particles were collected by filtration and dried under vacuum at room temperature. The amount of lipase adsorbed onto the resin was 6,000 lipase units g$^{-1}$.

6.38 mmoles of oleic acid (1.80 g) were stirred at 40° C. with 50 mg of the immobilised *Candida clyindracae* lipase catalyst. To initiate an esterification reaction, 0.4 mmoles (30 μl) of n-propanol were added to the mixture. Twenty-three further 0.267 mmoles (20 μl) aliquots were added at twenty minute intervals to give a total n-propanol addition of 6.54 mmoles. Samples were taken periodically from the reaction mixture for analysis of n-propanol content and n-propyl oleate formation.

In a control experiment, the entire 6.54 mmoles of n-propanol were added to the mixture of oleic acid and catalyst at the start of the reaction, and again samples were taken periodically for analysis.

The results given in Table 4 clearly show that n-propyl oleate was formed more rapidly in the experiment in which the n-propanol was added slowly in small aliquots to ensure that the n-propanol concentration in the reaction mixture remained low.

TABLE 4

| Reaction time (hours) | n-Propyl oleate formed | | n-Propanol content of reaction mixture | |
|---|---|---|---|---|
| | Example 4 (mmoles) | Control (mmoles) | Example 4 (mmoles) | Control (mmoles) |
| 1 | 0.66 | 0.02 | 0.3 | 6.5 |
| 2 | 1.22 | 0.06 | 0.5 | 6.5 |
| 4 | 2.59 | 0.11 | 0.7 | 6.4 |
| 6 | 3.90 | 0.16 | 1.0 | 6.4 |
| 8 | 4.27 | 0.20 | 2.3 | 6.3 |
| 24 | 5.77 | 0.54 | 0.8 | 6.0 |

EXAMPLE 5

Example 4 was repeated using iso-propanol instead of n-propanol. The results given in Table 5 again show that ester formation was much faster in the experiment in which the alcohol was added in small aliquots.

TABLE 5

| Reaction time (hours) | iso-Propyl oleate formed | | iso-Propanol content of reaction mixture | |
|---|---|---|---|---|
| | Example 5 (mmoles) | Control (mmoles) | Example 5 (mmoles) | Control (mmoles) |
| 1 | 0.45 | 0.00 | 0.5 | 6.5 |
| 2 | 0.98 | 0.01 | 0.8 | 6.5 |
| 4 | 1.91 | 0.01 | 1.4 | 6.5 |
| 7 | 2.72 | 0.02 | 3.0 | 6.5 |
| 24 | 4.05 | 0.05 | 2.5 | 6.5 |

I claim:

1. In a process for preparing an ester from an alcohol and fatty acid or glyceride thereof by enzyme-catalyzed conversion, the improvement which comprises mixing the fatty acid or glyceride thereof with a lipase catalyst and adding the alcohol to said mixture at such a rate that the alcohol concentration in the reaction mixture is kept below a molar ratio of 0.5 moles of alcohol per mole of fatty acid/acyl group whereby the rate of ester formation is increased.

2. A process according to claim 1, wherein the alcohol is added at such a rate that the molar ratio of alcohol to fatty acid/acyl group is below 0.25.

3. A process according to claim 1, wherein the alcohol is a $C_1$-$C_8$ alcohol.

4. A process according to claim 3, wherein the alcohol is a monohydric alcohol.

5. A process according to claim 1, wherein the fatty acid is a $C_2$-$C_{24}$ fatty acid.

6. A process according to claim 1, wherein the fatty acid glyceride is a triglyceride derived from $C_{10}$-$C_{24}$ fatty acids.

7. A process according to claim 5, wherein water of reaction is removed while esterification progresses.

8. A process according to claim 7, wherein said water is removed by dipping a cold surface in the gaseous phase of the reaction vessel.

9. A process according to claim 1, wherein the ester is prepared in the presence of water.

10. A process according to claim 7, wherein said water is removed by distillation.

11. A process according to claim 1 wherein the acid or glyceride thereof is oleic acid, butter oil or coconut oil and the alcohol is ethanol or propanol.

* * * * *